United States Patent [19]

Baker

[11] 4,330,530
[45] May 18, 1982

[54] ANTI-ARTHRITIC COMPOSITIONS AND METHOD USING GOLD SALTS AND ORGANOPHOSPHONATES

[75] Inventor: Bennie L. Baker, Cincinnati, Ohio

[73] Assignee: The Procter & Gamble Company, Cincinnati, Ohio

[21] Appl. No.: 219,052

[22] Filed: Dec. 22, 1980

[51] Int. Cl.³ ............... A61K 31/28; A61K 31/66; A61K 33/24

[52] U.S. Cl. ............... 424/131; 424/204; 424/290

[58] Field of Search ............ 424/204, 290, 131

[56] References Cited

U.S. PATENT DOCUMENTS

| | | | |
|---|---|---|---|
| 3,553,314 | 1/1970 | Francis | 424/49 |
| 3,553,315 | 1/1971 | Francis | 424/49 |
| 3,584,124 | 6/1971 | Francis | 424/49 |
| 3,584,125 | 6/1971 | Francis | 424/49 |
| 3,641,246 | 2/1972 | Francis | 424/49 |
| 3,662,066 | 5/1972 | Francis | 424/49 |
| 3,678,164 | 7/1972 | Francis | 424/49 |
| 3,683,080 | 8/1972 | Francis | 424/49 |

OTHER PUBLICATIONS

McCarty, D. J., *Arthritis & Allied Conditions*, Lea & Febiger (1979), pp. 355-364.
Jessop, *J. Rheumatol.* (Suppl. 5) 6:12-17 (1979).
Davis, *J. Rheumatol.* (Suppl. 5) 6:18-24 (1979).
Martendale, *The Extra Pharmacopoeia*, 26th Ed. (1975), pp. 477-479.
Francis et al., *Calc. Tiss. Res.*, 9:109-121 (1972).

*Primary Examiner*—Stanley J. Friedman
*Attorney, Agent, or Firm*—Steven J. Goldstein; Jack D. Schaeffer; Richard C. Witte

[57] ABSTRACT

Compositions comprising pharmaceutically-acceptable gold salts and organophosphonates, especially the geminal diphosphonates, useful in the treatment of arthritic conditions, are disclosed. The method of treating arthritic conditions using these compositions is also disclosed.

4 Claims, No Drawings

ANTI-ARTHRITIC COMPOSITIONS AND METHOD USING GOLD SALTS AND ORGANOPHOSPHONATES

BACKGROUND OF THE INVENTION

The present invention relates to pharmaceutical compositions used in the treatment of arthritic conditions, especially rheumatoid arthritis.

Rheumatic diseases are conditions in which pain and stiffness are prominent in portions of the musculoskeletal system, including the connective tissue. Arthritis is the general name used for such conditions when the joints, themselves, are the major seat of the rheumatic disease. Arthritis is one of the oldest known diseases. Chronic arthritis of the spine is known to have been present in the ape man of 2 million years ago, as well as in the Java and Lansing Men of 500 thousand years ago, and Egypian mummies dating to 8,000 B.C. See Osgood, R. B., *Amer. J. Med. Sci.*, 200: 429(1940). The Romans built extensive baths throughout their empire to aid in the treatment of arthritic diseases. Yet, in spite of this long history, the search for a safe and effective therapy for arthritic conditions continues. The importance of such work is underscored by the fact that there are over 20 million persons in the United States, today, suffering from some form of arthritis or related disease. Further, arthritis and rheumatism result in 27 million lost work days yearly, second only to heart disease as a cause of chronic limitation of ability to work.

Various gold salts have been recognized as an effective therapy for the treatment of rheumatoid arthritis. See McCarty, D. J., *Arthritis and Allied Conditions*, Lea & Febiger, 1979, pages 355-364. Gold was originally used to treat rheumatoid arthritis in the 1920's; this use was based on the empirical belief that since gold was of value in the treatment of tuberculosis, a chronic form of infectious disease, it might be efficacious in yet another chronic disorder suspected, at the time, of having an infectious etiology. Early work in the treatment of arthritic conditions using gold (Chrysotherapy) is summarized in Forestier, J., *J. Lab. Clin. Med.*, 20: 827(1935).

A major deterrent to the use of gold therapy is the frequent occurrence of side effects associated with such treatment; some tests indicate that 25 to 40 out of every 100 patients treated with gold salts will develop some degree of toxic reaction. One such side effect is renal toxicity, such as nephrosis. If renal toxicity side effects become apparent, it is necessary to discontinue the gold therapy and treat the side effect with corticosteroids. Thus, the occurrence of such side effects clearly curtails the usefulness of gold salt therapy in the treatment of arthritic conditions. Similar renal toxicity problems can occur where other metals are used to treat medical conditions, such as in the treatment of depression using lithium salts. From the foregoing, it is clear that it would be desirable to be able to formulate an effective treatment regimen for arthritic conditions, incorporating the use of gold salts, while minimizing the potential renal toxicity side effects of such treatment. Gold salt therapy also tends to inhibit bone mineralization; a treatment regimen which minimizes this effect would also be highly desirable. See Jessop, *Gold In The Treatment of Rheumatoid Arthritis-Why, When and How?*, J. Rheumatol. (Suppl. 5), 6: 12-17 (1979); Davis, *Undesirable Effects of Gold Salts*, J. Rheumatol. (Suppl. 5), 6: 18-24 (1979); and Martindale, *The Extra Pharmacopoeia*, 26th Edition, The Pharmaceutical Press, London, 1975, pages 477-479.

Organophosphonate compounds are reported in the literature as being useful in the treatment of anomalous mobilization and deposition of calcium phosphate salts (bone mineral) in humans and other animals; use of these compounds in the treatment of arthritis is specifically disclosed. See especially, U.S. Pat. Nos. 3,683,080, Francis, granted Aug. 8, 1972; 4,234,645, Gunther and Fleisch, issued Nov. 18, 1980; and 4,216,212, Flora and Francis, issued Aug. 5, 1980.

The article by Francis, Flora and King, entitled "The Effects of Disodium Ethane-1-Hydroxy-1,1-Diphosphonate on Adjuvant Induced Arthritis in Rats", appearing in *Calc. Tiss. Res.*, 9: 109-121 (1972) discloses the use of a diphosphonate material in the treatment of arthritis in rats and mentions the use of phosphonates to inhibit inflammatory erosion in rat cartilage.

It is an object of the present invention to provide pharmaceutical compositions, comprising organophosphonates and gold salts, which are effective in the treatment of arthritic conditions while minimizing the renal toxicity and inhibition of bone mineralization which can accompany treatment with gold salts.

It is a further object of the present invention to provide a method for treating arthritic conditions utilizing combinations of organophosphonates and gold salts.

SUMMARY OF THE INVENTION

The present invention encompasses compositions and methods for treating arthritic conditions in animal tissue, especially in humans. The invention provides effective drug combination compositions and therapy, and is based on the use of pharmacologically-active phosphonate compounds together with pharmaceutically-acceptable gold salts useful in the treatment of arthritic conditions.

The compositions of this invention comprise a safe and effective amount of an organophosphonate compound, particularly a geminal diphosphonate such as dichloromethane diphosphonic acid, together with a safe and effective amount of a pharmaceutically-acceptable gold salt useful in the treatment of arthritic conditions, such as gold sodium thiomalate. The compounds act in concert to provide effective treatment of the arthritic condition while minimizing or eliminating side effects, such as renal toxicity and the inhibition of bone mineralization, which frequently accompany therapy with gold salts.

The invention also encompasses treatment regimens for arthritic conditions comprising administering to a human or animal in need of such treatment a safe and effective amount of an organophosphonate compound and a safe and effective amount of a pharmaceutically-acceptable gold salt useful in the treatment of arthritic conditions.

DETAILED DESCRIPTION OF THE INVENTION

The compositions and treatment regimens of this invention employ: (1) a safe and effective amount of a pharmaceutically-acceptable gold salt useful in the treatment of arthritic conditions; and (2) a safe and effective amount of a pharmaceutically-acceptable organophosphonate compound.

By "safe and effective amount of gold salt", as used herein, is meant sufficient gold salt compound to treat an arthritic condition, such as rheumatoid arthritis, at a reasonable benefit/risk ratio attendant with any medical treatment, when used in the manner of this invention. Within the scope of sound medical judgment, the dosage of gold salt will vary with the particular condition being treated, the severity of the condition, the duration of the treatment, the physical and medical characteristics of the patient, and the specific gold salt and phosphonate compounds employed.

By "safe and effective amount of phosphonate compound", as used herein, is meant a sufficient amount of the phosphonate compound to effectively treat the bone erosion which accompanies arthritic conditions and, in addition, to minimize gold-induced renal abnormalities and inhibition of bone mineralization, at a reasonable benefit/risk ratio attendant with any medical treatment. Within the scope of sound medical judgment, the dosage of phosphonate will vary with the particular condition being treated, the severity of the condition, the duration of the treatment, the physical and medical characteristics of the patient, and the specific phosphonates and gold salts employed.

By "pharmaceutically-acceptable", as used herein, is meant that the drug compounds and other ingredients used in the present compositions and methods of treatment are suitable for use in contact with the tissues of humans and lower animals without undue toxicity, irritation, allergic response, and the like, commensurate with a reasonable benefit/risk ratio.

The term "administration" of the compounds and compositions herein includes systemic dosage, as by injection (especially parenterally), intravenous infusion, suppositories and oral administration thereof, as well as topical application of the compounds and compositions to the afflicted situs.

By the term "comprising", as used herein, is meant that various other, compatible drugs and medicaments, as well as inert ingredients, can be conjointly employed in the compositions and processes of this invention, as long as the critical phosphonate compounds and gold salts are used in the manner disclosed.

By "compatible" herein is meant that the components of the compositions are capable of being comingled without interacting in a manner which would substantially decrease the efficacy of the total compositions under ordinary use situations.

By "carrier", as used herein, is meant a liquid, fluid or solid material which can optionally be used to provide finished compositions for systemic or topical administration.

All percentages herein are by weight, unless otherwise specified.

Any pharmaceutically-acceptable gold salt, useful in the treatment of arthritic conditions, may be used in the present invention. A number of such gold compounds have been synthesized and are effective in the treatment of arthritic conditions; these include, but are not limited to, gold sodium thiomalate, gold sodium thiosulfate, triethylphosphine gold (e.g., Auranofin, which is especially adapted for oral administration, commercially available from Smith, Kline and French), gold sodium thioglucose, and mixtures of these components. The gold salts most commonly used in the United States for the treatment of arthritic conditions include gold sodium thiomalate, available commercially as Myochrysine from Merck Sharpe and Dohme as an aqueous solution of 50% gold for intramuscular injection, and Aurothioglucose (gold sodium thioglucose), commercially available as Solganal from Schering as a water-soluble 50% gold preparation for intramuscular use prepared as a suspension in oil. Gold sodium thiomalate is especially preferred for use in the present invention.

Gold salts are generally administered to arthritic patients on a dosing schedule which retains the therapeutic benefits of the gold salts while minimizing the severity of potential toxic reactions. In such a dosing regimen, the initial dose is 10 milligrams of gold per week (e.g., by intramuscular injection), raised step-wise over the next 2 to 3 weeks to 25 milligrams and then 50 milligrams. These small initial doses are used to identify patients who might be susceptible to gold toxicity. If there are no side effects, 50 milligram dosages are given weekly for the next 20 weeks. Treatment with the gold salts is generally continued for a prolonged period to prevent relapses. In the usual maintenance program, gold is given as 50 milligram injections at increasingly greater intervals, initially every 2 weeks for 4 to 8 injections, then every 3 weeks for 4 to 6 injections, and monthly thereafter for an indefinite period. If there is a return of symptoms, then weekly injections of 50 milligrams are reinstituted. The applicability of this dosing program to particular cases depends upon numerous factors, including the medical and physical condition of the patient, the severity of the illness, and the phosphonate materials being administered; in general, the dosages can range from 5 milligrams to 200 milligrams of gold salt per week, although the preferred dosages tend to be between about 10 milligrams and 75 milligrams of gold salt per week. The compositions of the present invention may contain from about 1 milligram to about 200 milligrams, preferably from about 2 to about 75 milligrams, of gold salt, depending upon the frequency with which the compositions are to be taken and how they are to be administered (e.g., orally, or by intramuscular injection).

The organophosphonate compounds (or more succinctly, "phosphonates") employed in the present invention are characterized by the phosphonate moiety ($—PO_3M_2$, wherein M represents H or a pharmaceutically-acceptable cation or ester group). The phosphonates herein are organophosphonates, i.e., the phosphonate moiety is attached to a carbon atom by a carbon-phosphorus bond (C-P bond). The carbon atom, in turn, can be bonded to other hydrocarbyl groups, e.g., alkyl phosphonates, or to hydrogen atoms, e.g., methane phosphonates, halogen atoms, e.g., dichloromethane diphosphonates, or to mixed hydrocarbyl groups, hydrogen atoms or other substituents, e.g., haloalkyl phosphonates. The hydrocarbyl groups can be substituted or unsubstituted alkyl (including cycloalkyl), aryl (including heteroaryl) and the like. Substitutent groups on the alkyl or aryl hydrocarbyl moiety can be, for example, additional phosphonate moieties; halogens, especially chlorine; carboxyl; esterified carboxyl; hydroxyl; amino; amido; and the like. Preferred for use herein are organophosphonates having more than one $C-PO_3M_2$ group; disphosphonates, especially geminal diphosphonates characterized by the group

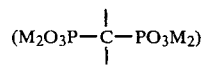

are most highly preferred.

Typical phosphonate compounds useful herein are selected from those having the formula

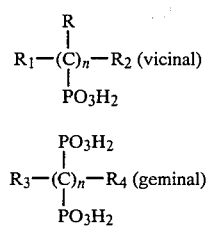

$$R_1-(C)_n-R_2 \text{ (vicinal)} \quad \text{with } R \text{ and } PO_3H_2 \text{ substituents} \quad (I)$$

$$R_3-(C)_n-R_4 \text{ (geminal)} \quad \text{with two } PO_3H_2 \text{ substituents} \quad (II)$$

wherein n is an integer from 1 to about 10 and the substitutent groups are H, alkyl, aryl, alkenyl, and the like. Examples of Type (I) phosphonates are those wherein R, $R_1$ and $R_2$ are each hydrogen, alkyl, $-CH_2OH$, or as noted for groups $R_3$ and $R_4$. Examples of Type (II) phosphonates are those wherein $R_3$ is hydrogen, alkyl containing from 1 to about 20 carbon atoms, alkenyl containing from 2 to about 20 carbon atoms, aryl (e.g., phenyl or naphthyl), phenylethenyl, benzyl, halogen (e.g., chlorine, bromine, or fluorine), amino, substituted amino (e.g., dimethylamino, diethylamino, N-hydroxy-N-ethylamino, or acetylamino), $-CH_2COOH$, $-CH_2PO_3H_2$, $-CH(PO_3H_2)(OH)$, or $-CH_2CH(PO_3H_2)_2$; $R_4$ is hydrogen, lower alkyl (e.g., methyl, ethyl, propyl, or butyl), amino, benzyl, halogen, (e.g., chlorine, bromine, or fluorine), hydroxyl, $-CH_2COOH$, $-CH_2PO_3H_2$, or $-CH_2CH_2PO_3H_2$, or a pharmaceutically-acceptable salt thereof, such as alkali metal (e.g., sodium or potassium), alkaline earth metal (e.g., calcium or magnesium), non-toxic heavy metal (e.g., stannous or indium), and ammonium or low molecular weight, substituted ammonium (e.g., mono-, di-, or triethanolammonium) salts. It will also be appreciated that groups R, $R_1$ and $R_2$ and groups $R_3$ and $R_4$ can be cycloalkyl, heterocyclic or can be joined in ring structures, said rings being carbocyclic or heterocyclic.

Non-limiting examples of phosphonates of the above type (I) include propane-1,2,3-triphosphonic acid; butane-1,2,3,4-tetraphosphonic acid; hexane-1,2,3,4,5,6,-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid; nonane-1,2,3,4,5,6,7,8,9-nonaphosphonic acid; decane-1,2,3,4,5,6,7,8,9,10-decaphosphonic acid; and the pharmaceutically-acceptable salts of these acids, e.g., sodium, potassium, calcium, magnesium, ammonium, triethanolammonium, diethanolammonium, and monoethanolammonium salts.

Among the operable phosphonates encompassed by type (II) are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; dichloromethanediphosphonic acid; nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphonoprop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-hydroxyethyl)-aminomethanediphosphonic acid; N-acetylaminomethanediphosphonic acid; aminomethanediphosphonic acid; and the pharmaceutically-acceptable salts of these acids, e.g., sodium, potassium, calcium, magnesium, stannous, indium, ammonium, triethanolammonium, diethanolammonium, and monoethanolammonium salts.

Mixtures of any of the foregoing phosphonic acids and/or salts can be used in the practice of this invention. The geminal diphosphonates are most preferred for use herein; preferred members of this group include ethane-1-hydroxy-1,1-diphosphonic acid, dichloromethane diphosphonic acid, methanediphosphonic acid, pharmaceutically-acceptable salts of these acids, and mixtures thereof.

Ethane-1-hydroxy-1,1-diphosphonic acid is a preferred geminal diphosphonate for use herein; its preparation is disclosed in U.S. Pat. No. 3,400,149, Quimby, issued Sept. 3, 1968, incorporated herein by reference. This compound has the molecular formula $CH_3C(OH)(PO_3H_2)_2$ and according to the nomenclature by radicals, the acid may also be named 1-hydroxyethylidene diphosphonic acid. The most readily crystallizable salt of this acid is obtained when two or three of the acid hydrogens are replaced by sodium. Preferred salts for the purpose of this invention are the trisodium hydrogen salt, the disodium dihydrogen salt, and/or mixtures thereof.

Dichloromethanediphosphonic acid is an especially preferred geminal diphosphonate for use herein. This compound has the molecular formula $Cl_2C(PO_3H_2)_2$, and is abbreviated $Cl_2MDP$. The dichloromethanediphosphonates, especially the sodium salts of $Cl_2MDP$, are readily prepared and are most preferred for use in the practice of this invention. Methanediphosphonic acid and its salts are also preferred for use herein; the compounds and the methods for preparing those compounds are described in detail in U.S. Pat Nos. 3,213,030, Diehl, granted Oct. 19, 1965 and 3,251,907, Roy, granted May 17, 1966, both of which are incorporated herein by reference.

Other phosphonate compounds, examples of which are given below, are well-known in the art. Thus, methane-hydroxydiphosphonic acid and related compounds are described in U.S. Pat. No. 3,422,137, Quimby, issued Jan. 14, 1969; ethane-1,1,2-triphosphonic acid and related compounds are described in U.S. Pat. No. 3,551,339, Quimby, issued Dec. 29, 1970; propane-1,1,3,3-tetraphosphonic acid and related compounds are described in U.S. Pat. No. 3,400,176, Quimby, issued Sept. 3, 1968; pentane-2,2-diphosphonic acid and related compounds are described in Kosolopoff, J. Amer. Chem. Soc., 75: 1500 (1953); propane-1,2,3-triphosphonic acid and salts thereof are described in U.S. Pat. No. 3,743,688, Nicholson and Campbell, issued July 3, 1973; butane-1,2,3,4-tetraphosphonic acid and salts thereof are described in U.S. Pat. No. 3,755,504, Nicholson and Campbell, issued Aug. 28, 1973; the higher aliphatic vicinal polyphosphonates and salts thereof are described in U.S. Pat. No. 3,584,035, Nicholson and Campbell, issued June 8, 1971; substituted ethane diphosphonic acids and salts and esters thereof are described in U.S. Pat. No. 3,940,436, Kerst, issued Feb. 24, 1976; halogenated and hydroxylated geminal diphosphonates are disclosed in U.S. Pat. No. 3,944,599, Kerst; phosphonobutane tri- and tetracarboxylic acid are disclosed in U.S. Pat. No. 3,886,204, Geffers, et al.; and various amino phosphonate compounds are described in German specification No. 2,343,146 (Mar. 6, 1975), German specification No. 2,360,711 (June 12, 1975), German specification No. 2,360,719 (June 6, 1975). The disclosures of all of the above patents and articles are incorporated herein by reference.

While any pharmaceutically-acceptable salt of the phosphonates can be used in the practice of this invention, the sodium salts are preferred. Various pharmaceutical cations such as potassium, ammonium, mono-, di-, and triethanolammonium, and mixtures thereof, are also suitable for use as counterions in the salts, provided caution is observed in regulating the total intake of cation species in the salt compositions. Such salts can be prepared by any suitable method involving neutralization of the parent phosphonic acid.

The present invention in most conveniently practiced by administering a single composition which comprises a mixture of gold salt and phosphonate. In an alternate mode, the dosage regimen can consist of separate administration of the two agents; this latter approach is less convenient, but may be desirable based on the pharmacological properties of the particular compounds administered or the needs of a particular patient.

Compositions comprising the gold salt and phosphonate components can be administered parenterally in aqueous solution by subcutaneous, intradermal, intramuscular or intravenous injection.

When administered orally, the phosphonate compounds herein are only about 10% absorbed through the gut, the rest being excreted. Accordingly, oral compositions typically contain an excess of the phosphonate material over that which can be effectively used in an injectable form to account for the low absorption. Dosage forms of the present invention will, generally, contain from about 50 milligrams to about 500 milligrams of the phosphonate compound, preferably, a geminal disphosphonate, such as dichloromethanediphosphonic acid, ethane-1-hydroxy-1,1-diphosphonic acid, methanediphosphonic acid, or a pharmaceutically-acceptable salt of these materials. Of course, the total dosage of the compositions herein will be decided by the attending physician and will be determined by such factors as the type and severity of the arthritic condition being treated, the age and weight of the patient, the medical history of the patient, and like factors well-known in the medical art. In general, treatment regimens according to the present invention will call for the administration of from about 200 milligrams to about 2000 milligrams per day of the diphosphonate materials.

For purposes of oral administration, compositions can be formulated as capsules, tablets or granules. For treatment of non-human animals, compositions are preferably incorporated in animal feeds, feed supplements or feed concentrates.

Compositions comprising the gold salts and phosphonate materials can be administered, per se, or, more preferably, in combination with a solid or liquid filler, diluent or encapsulating substance as a pharmaceutical carrier, e.g., materials commonly used in a manufacture of tablets, capsules, elixirs, and the like. Some examples of the substances which can serve as pharmaceutically-acceptable carriers include pyrogen-free water; water-alcohol mixtures; saline; sugars, such as lactose, glucose and sucrose; starches, such as corn starch and potato starch; cellulose and its derivatives, such as sodium carboxymethyl cellulose, ethyl cellulose, and cellulose acetate; powdered gums; malt; gelatin; stearic acid; calcium sulfate; vegetable oils, such as peanut oil and cottonseed oil; mineral oil; polyols, such as propylene glycol, glycerin, sorbitol, mannitol, and polyethylene glycol; agar, alginic acid; as well as other non-toxic, compatible substances used in pharmaceutical formulations. Wetting agents and lubricants, such as sodium lauryl sulfate, as well as coloring agents, flavoring agents and preservatives can also be present.

Renal toxicity side effects may also be present when metal salts, aside from gold, are used in the treatment of medical conditions. Thus, when lithium salts, such as lithium carbonate, lithium chloride, lithium citrate, lithium sulfate, and mixtures of these materials, are used in the treatment of manic depressive conditions renal toxicity can result. The administration of organophosphonate compounds together with these lithium salts reduces the renal toxicity side effects which may accompany such treatment. Compositions comprising a safe and effective amount of the pharmaceutically-acceptable lithium salts together with organophosphonate compounds, particularly geminal diphosphonates, in an amount safe and effective to minimize or eliminate the renal toxicity side effects, would be used in this manner.

The compositions herein can be prepared by standard formulation and tableting techniques used in the pharmaceutical industry. The following examples illustrate the present compositions and their use, but are not intended to be limiting of the scope of the invention.

EXAMPLE I

Capsules, having the following formulation, are prepared by conventional methods.

| Ingredient | mg. per Capsule |
|---|---|
| Ethane-1-hydroxy-1,1-diphosphonic acid | 400 |
| Triethyl phosphine gold (e.g., Auranofin) | 7 |

A capsule of the type above is administered orally once daily and is effective in treating patients having rheumatoid arthritis while minimizing the renal toxicity and bone mineralization inhibition side effects which can accompany gold salt therapy.

The composition of Example I may also be formulated as a tablet, using conventional tableting techniques and agents.

In the composition of Example I, the ethane-1-hydroxy-1,1-diphosphonic acid is replaced, in whole or in part, by equivalent amounts of ethane-1-hydroxy-1,1-diphosphonic acid, sodium salt form; dichloromethanediphosphonic acid or the sodium salts thereof; methanediphosphonic acid or the sodium salts thereof, and equivalent results are secured. The compositions are also usefully formulated using 200 mg or 500 mg of the phosphonate component per capsule.

In the capsules of Example I, the gold sodium thiomalate is replaced, in whole or in part, by equivalent amounts of gold sodium thiosulfate, gold sodium thiomalate, or gold sodium thioglucose, in a form suitable for oral administration, and equivalent results are secured.

EXAMPLE II

Capsules, having the composition given below, are prepared by conventional methods.

| Ingredient | mg per Capsule |
|---|---|
| Dichloromethanediphosphonic acid | 200 |
| Triethylphosphine gold (e.g., Auranofin) | 4 |

A capsule of this type is administered orally twice daily, and is effective in the treatment of arthritic conditions.

In the composition of Example II, the dichloromethanediphosphonic acid is replaced, in whole or in part, by an equivalent amount of dichloromethanediphosphonic acid, sodium salt form, and equivalent results are secured. The compositions are also usefully formulated using 400 mg or 500 mg of the phosphonate component per capsule.

In the capsules of Example II, the triethylphosphine gold is replaced, in whole or in part, by gold sodium thiomalate, gold sodium thiosulfate, gold sodium thioglucose, in a form suitable for oral administration and equivalent results are secured.

EXAMPLE III

A composition for intramuscular injection is prepared by blending the following ingredients:

| Ingredient | mg. per Dose |
|---|---|
| Dichloromethanediphosphonic acid, disodium salt | 500 |
| Gold sodium thiomalate | 50 |
| Pyrogen-free water | Balance |

The composition of Example III is administered by intramuscular injection once a week to a patient having rheumatoid arthritis. Over the course of treatment, the bone erosive activity associated with the arthritic condition decreases, the bone does not tend to demineralize, and no renal toxicity side effects are seen.

In the composition of Example III, the diphosphonate material is replaced, in whole or in part, by an equivalent amount of ethane-1-hydroxy-1,1-diphosphonic acid, methanediphosphonic acid, or pharmaceutically-acceptable salts of these compounds, and equivalent results are obtained.

In the composition of Example III, the gold sodium thiomalate is replaced, in whole or in part, by equivalent amounts of gold sodium thiosulfate, triethylphosphine gold, or gold sodium thioglucose and equivalent results are secured.

The unit dosage composition of Example III may also be formulated with variations in the diphosphonate or gold salt levels included, depending upon the particular dosages to be administered at a given time in the course of treatment.

EXAMPLE IV

A patient having rheumatoid arthritis is given one intramuscular injection containing 50 mg of gold sodium-thiomalate per week and one tablet containing 500 mg of dichloromethane diphosphonic acid (disodium salt) daily. This course of treatment is continued for six months and the gold salt dosage is then reduced to maintenance levels. The bone erosive activity associated with the arthritic condition is found to decrease; further, no bone demineralization activity or renal toxicity is seen.

EXAMPLE V

The effect of the present invention on renal toxicity was demonstrated in the following manner. 135 Male Charles Rivers CD (Sprague-Dawley) rats, each weighing between 125 and 175 grams were divided, at random, into 9 groups of equal size. Each group was placed under a treatment regimen as described in the table below for a 91 day period. The dichloromethanediphosphonate ($Cl_2MDP$), sodium salt, was administered by subcutaneous ventral flank injections, while the gold sodium thiomalate (GST) was administered by intramuscular injections, alternating each week between the left and right thigh muscle.

| Group | Treatment |
|---|---|
| 1 | Vehicle control (0.5% benzyl alcohol + sterile isotonic saline) |
| 2 | 2 mg/kg $Cl_2MDP$ + 0.5% benzyl alcohol |
| 3 | 10 mg/kg $Cl_2MDP$ + 0.5% benzyl alcohol |
| 4 | 2 mg/kg GST + sterile isotonic saline |
| 5 | 10 mg/kg GST + sterile isotonic saline |
| 6 | 2 mg/kg $Cl_2MDP$ + 2 mg/kg GST |
| 7 | 2 mg/kg $Cl_2MDP$ + 10 mg/kg GST |
| 8 | 10 mg/kg $Cl_2MDP$ + 2 mg/kg GST |
| 9 | 10 mg/kg $Cl_2MDP$ + 10 mg/kg GST |

At the end of the treatment period, the rats were sacrificed, necropsied, and the effects of the treatment on the rats' kidneys were evaulated in terms of tubular degeneration and the presence of megalocytes. Megalocytes are a regenerative phenomenon associated with heavy metal nephrotoxicity. The severity of lasions observed was noted and graded on a scale of 1–4. These results are summarized in Tables 1 and 2, below.

TABLE 1

Tubular Degeneration (#animals/lesion severity) for Various Combinations of $Cl_2MDP$ and GST

| Dose of $Cl_2MDP$ (mg/kg) | Dose of GST (mg/kg) | | |
|---|---|---|---|
| | 0 | 2 | 10 |
| 0 | 15/NC | 15/NC | 9/1, 6/3 |
| 2 | 15/NC | 15/NC | 13/NC, 2/1 |
| 10 | 13/NC, 1/1, 1/2 | 14/NC, 1/1 | 6/NC, 3/1, 3/2, 3/3 |

TABLE 2

Megalocytes (#animals/lesion severity) for Various Combinations of $Cl_2MDP$ and GST

| Dose of $Cl_2MDP$ (mg/kg) | Dose of GST (mg/kg) | | |
|---|---|---|---|
| | 0 | 2 | 10 |
| 0 | 15/NC | 3/2, 12/3 | 4/2, 11/3 |
| 2 | 15/NC | 14/2, 1/3 | 9/2, 6/3 |
| 10 | 15/NC | 8/2, 7/3 | 3/2, 12/3 | lesion severity: 1 = minimal, 2 = mild, 3 = moderate, 4 = marked; NC-indicated change not observed The data summarized above indicate that the combinations of the two agents exhibit a positive interaction on GST related renal damage. Tables 1 and 2 show that increasing doses of GST increases the number of incidents and the severity of renal tubular degeneration and megalocytosis, respectively. Cl₂MDP treatments on the other hand, had no significant effect on these parameters. When Cl₂MDP and GST treatments were administered concurrently, both the number of instances and the severity of GST-induced renal toxicity, especially in terms of megalocytosis, were reduced.

Tibias from animals in each of the groups, described above, were isolated and analyzed to determine their fat-free dry weights, ash weights, and calcium and phosphorus contents. The calcium and phosphorous levels of these bones are summarized in the tables, below.

TABLE 3

Mean Percent Calcium for Various Combinations of Cl₂MDP and GST

| Dose of Cl₂MDP (mg/kg) | Dose of GST (mg/kg) | | |
|---|---|---|---|
| | 0 | 2 | 10 |
| 0 | 24.3 | 23.8+ | 23.8+ |
| 2 | 24.7* | 24.6* | 24.5* |
| 10 | 24.5 | 24.8* | 24.8* |

TABLE 4

Mean Percent Phosphorus for Various Combinations of Cl₂MDP and GST

| Dose of Cl₂MDP (mg/kg) | Dose of GST (mg/kg) | | |
|---|---|---|---|
| | 0 | 2 | 10 |
| 0 | 12.5 | 12.2+ | 12.2+ |
| 2 | 12.5 | 12.6* | 12.4* |
| 10 | 12.4 | 12.4* | 12.3* |

*Statistically different from group with no Cl₂MDP at the given GST dose level
+Statistically different from group with no GST at the given Cl₂MDP dose level.

The above data indicate that the combination therapy of the present invention exhibited a positive interaction on the calcium and phosphorus content of the bone. In the absence of Cl₂MDP, GST treatment caused a statistically significant lower calcium and phosphorus content in bone. However, when Cl₂MDP and GST treatment were administered concurrently, changing levels of GST had no statistically significant effect on the calcium or phosphorus content.

What is claimed is:

1. A method for treating arthritic conditions comprising administering to a human or animal in need of such treatment a safe and effective amount, not less than about 200 mg. per day, of an organophosphonate compound and a safe and effective amount, within the range from about 5 to about 200 mg. per week, of a pharmaceutically-acceptable gold salt useful in the treatment of such conditions, wherein the organophosphonate compound is selected from the group consisting of

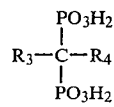

wherein $R_3$ is hydrogen, alkyl containing from 1 to about 20 carbon atoms, alkenyl containing from 2 to about 20 carbon atoms, aryl, phenylethenyl, benzyl, halogen, amino, substituted amino, —CH₂COOH, —CH₂PO₃H₂, —CH(PO₃H₂) (OH), or —CH₂CH(PO₃H₂)₂; $R_4$ is hydrogen, lower alkyl, amino, benzyl, halogen, hydroxyl, —CH₂COOH, —CH₂PO₃H₂, or —CH₂CH₂PO₃H₂, and the pharmaceutically-acceptable salts thereof, and wherein the gold salt is selected from the group consisting of gold sodium thiomalate, gold sodium thiosulfate, triethylphosphine gold, gold sodium thioglucose and mixtures thereof.

2. A method according to claim 1 wherein the organophosphonate compound is selected from the group consisting of dichloromethanediphosphonic acid, ethane-1-hydroxy-1,1-diphosphonic acid, methanediphosphonic acid, pharmaceutically-acceptable salts of these acids, and mixtures thereof.

3. A pharmaceutical composition in unit dosage form comprising from about 50 mg. to about 500 mg. of an organophosphonate compound selected from the group consisting of

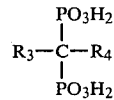

wherein $R_3$ is hydrogen, alkyl containing from 1 to about 20 carbon atoms, alkenyl containing from 2 to about 20 carbon atoms, aryl, phenylethenyl, benzyl, halogen, amino, substituted amino, —CH₂COOH, —CH₂PO₃H₂, —CH(PO₃H₂) (OH), or —CH₂CH(PO₃H₂)₂; $R_4$ is hydrogen, lower alkyl, amino, benzyl, halogen, hydroxyl, —CH₂COOH, —CH₂PO₃H₂, or —CH₂CH₂PO₃H₂, and the pharmaceutically-acceptable salts thereof, and from about 1 mg. to about 200 mg. of a gold salt selected from the group consisting of gold sodium thiomalate, gold sodium thiosulfate, triethylphosphine gold, gold sodium thioglucose, and mixtures thereof.

4. A composition according to claim 3 wherein the organophosphonate compound is selected from the group consisting of dichloromethanediphosphonic acid, ethane-1-hydroxy-1,1-diphosphonic acid, methanediphosphonic acid, and the pharmaceutically-acceptable salts of these acids.

* * * * *